(12) United States Patent
Lloyd et al.

(10) Patent No.: US 8,709,459 B2
(45) Date of Patent: *Apr. 29, 2014

(54) TRIPLE-ACTION PEST CONTROL FORMULATION AND METHOD

(75) Inventors: Jeffrey Douglas Lloyd, Knoxville, TN (US); Janet Louise Kintz-Early, Knoxville, TN (US)

(73) Assignee: Nisus Corporation, Rockford, TN (US)

( * ) Notice: Subject to any disclaimer, the term of this patent is extended or adjusted under 35 U.S.C. 154(b) by 1841 days.

This patent is subject to a terminal disclaimer.

(21) Appl. No.: 11/627,069

(22) Filed: Jan. 25, 2007

(65) Prior Publication Data

US 2007/0122442 A1 May 31, 2007

Related U.S. Application Data

(63) Continuation-in-part of application No. 10/928,510, filed on Aug. 27, 2004, and a continuation-in-part of application No. 11/279,459, filed on Apr. 12, 2006.

(51) Int. Cl.
*A01N 25/12* (2006.01)
*A01N 59/14* (2006.01)

(52) U.S. Cl.
USPC .......... 424/409; 424/84; 424/405; 424/410; 424/658; 424/660; 514/432; 514/453

(58) Field of Classification Search
None
See application file for complete search history.

(56) References Cited

U.S. PATENT DOCUMENTS

| | | | |
|---|---|---|---|
| 4,287,183 A | 9/1981 | Hagerman et al. | |
| 4,518,580 A | 5/1985 | Pasarela | |
| 4,581,378 A | 4/1986 | Lazar et al. | |
| 4,996,053 A | 2/1991 | Hatcher | |
| 5,104,664 A | 4/1992 | Palmere et al. | |
| 5,296,240 A | 3/1994 | Palmere et al. | |
| 5,592,774 A | 1/1997 | Galyon | |
| 5,876,740 A * | 3/1999 | Schwalenberg et al. | 424/408 |
| 6,007,832 A | 12/1999 | Stapleton | |
| 6,368,529 B1 | 4/2002 | Manning et al. | |
| 6,426,095 B2 | 7/2002 | Palmere et al. | |

(Continued)

FOREIGN PATENT DOCUMENTS

AU 2003203735 A1 11/2003
DE 101 32 532 A1 2/2003

(Continued)

OTHER PUBLICATIONS

Genesis Laboratories, Inc. Wellington, Co., Standard House Mouse Acute Dry Bait Laboratory Test Method, OPP Designation, 1:210 revision No. 9 USEPA—"EPA Challenge Diet" date unknown, Apr. 2006.

(Continued)

*Primary Examiner* — Neil Levy
(74) *Attorney, Agent, or Firm* — Luedeka Neely Group, P.C.; J. David Gonce

(57) ABSTRACT

The present disclosure provides a triple-action pest control formulation for controlling rodents, insects, and terrestrial mollusks, the formulation including: a first active ingredient which is a rodenticide; a second active ingredient which is both an insecticide and a molluscicide; an optional attractant; and a carrier matrix. The present disclosure also provides a method of controlling rodents, insects, and terrestrial mollusks by applying the triple action pest control formulation to a target area or supplying the formulation in a bait station.

25 Claims, 3 Drawing Sheets

(56) References Cited

U.S. PATENT DOCUMENTS

| | | |
|---|---|---|
| 6,630,174 B2 | 10/2003 | Palmere et al. |
| 6,645,949 B1 | 11/2003 | Nigg et al. |
| 6,689,796 B1 | 2/2004 | Johnson et al. |
| 6,896,908 B2 | 5/2005 | Lloyd et al. |
| 6,984,662 B2 | 1/2006 | Cottrell et al. |
| 7,067,142 B2 * | 6/2006 | Yonker et al. ............ 424/406 |
| 7,163,974 B2 | 1/2007 | Manning et al. |
| 7,223,415 B1 | 5/2007 | Malone et al. |
| 2002/0010156 A1 | 1/2002 | Kennedy |
| 2003/0215481 A1 | 11/2003 | Borchert |
| 2005/0196628 A1 | 9/2005 | Lloyd et al. |
| 2006/0045898 A1 | 3/2006 | Lloyd |
| 2006/0057178 A1 | 3/2006 | Borchert |
| 2007/0240360 A1 | 10/2007 | Lloyd et al. |

FOREIGN PATENT DOCUMENTS

| | | |
|---|---|---|
| EP | 0 248 991 A2 | 12/1987 |
| JP | 62195301 | 8/1987 |
| WO | WO 92/22205 | 12/1992 |
| WO | WO 95/35029 | 12/1995 |
| WO | WO 00/11948 | 3/2000 |
| WO | WO 00/15033 | 3/2000 |
| WO | WO 01/17348 A1 | 3/2001 |
| WO | WO 01/87559 A1 | 11/2001 |
| WO | WO 02/06417 A1 | 1/2002 |

OTHER PUBLICATIONS

ANON 1989 Merck Index, "An Encyclopedia of Chemicals, Drugs and Biologicals", 11th Edition Budavari S(ed) Merck & Co. Inc.

Williams D F (1990) "Effects of Fenoxycarb Baits on Laboratory Colonies of the Pharaohs Ant *Monomorium pharaonis*". In Applied Myrmecology—A World Perspective '676-683. Ed Jaffe K. & Cedeno A Westview Press San Francisco & Oxford.

Milanez, J.M.; Chiaradia, L.A., Efficiency of Baits with Boric Acid to Control Sarasinula Linguaaformis (Semper, 1885) (Mollusca, Veroniceeidae), Pesquisa Agropecuaria Gaucha, vol. 5, No. 2 pp. 351-355 (1999) (1 page Abstract).

* cited by examiner

TRIPLE-ACTION PEST CONTROL FORMULATION AND METHOD

CROSS-REFERENCE TO RELATED APPLICATIONS

This application is a continuation-in-part of copending application Ser. No. 10/928,510, filed Aug. 27, 2004, entitled "Weather Resistant Granular Slug, Snail and Insect Bait" and Ser. No. 11/279,459, filed Apr. 12, 2006, entitled "Dual-Action Pest Control Formulation and Method."

FIELD

This invention relates to the field of pest control. More particularly, this invention relates to a formulation for control and/or elimination of multiple species of diverse household pests.

BACKGROUND

Residential and commercial properties are often beset by diverse species of animal pests. For example, rodents, such as mice and rats, are common pests that can cause significant damage to property and products, and can be disease carriers. Similarly, arthropods, such as insects including roaches and ants, can cause considerable property damage and can also be disease carriers. Rodents and insects can often coexist in the same environment, and many environments having a rodent infestation also have an insect infestation.

Despite the coexistence of rodents and insects, traditional pest control generally involves a separate treatment for attempting to control each pest. When traditional pest control formulations are set out, the types of active ingredients used to control one type of organism are typically different from those that will work for another type of organism. For example, bromadiolone is a common active ingredient for control of rodents, but it has no insecticidal properties. Similarly, pyrethroids are good examples of insecticides that have no rodenticidal performance.

The exclusive nature of these active ingredients can be problematic. For example, rodenticides may be consumed by roaches before rodents have a chance to consume them. In such situations, the roach population increases and there is no impact on the rodent population, so the infestation of both populations can actually become worse than it was prior to the attempted pest control intervention. The converse is also possible. Insect bait systems can attract and increase rodent populations because they are not harmful to rodents, and this results in both insect and rodent pest populations proliferating.

A third form of pest is terrestrial mollusks, such as slugs and snails, which are capable of extensively damaging plants including flowers, vegetables, and some trees and shrubs. Not only can terrestrial mollusks be quite damaging, existing baits designed to exterminate them often do not always perform well in the natural environments of mollusks, which is often permanently moist or frequently wet. Existing baits also sometimes lose their physical integrity under such circumstances or lose their efficacy upon prolonged exposure to moisture, sunlight, or both. In addition, many slugs and snails live in environments where damaging insects are also present. Further, some known molluscides, such as metaldehyde, are highly toxic to humans, to domestic pets, and to birds. Slugs and snails and baits for slugs and snails can also pose the same reciprocal problems as insecticides and rodenticides, i.e., slugs and snails may eat baits designed for other target pests, or the slug and snail baits may be eaten by other target pests or by non-target species. This is both a direct problem when pets or children directly eat slug and snail baits, and also is an indirect problem when the poisoned slugs or snails are themselves eaten by non-target species such as birds, small mammals, pets or even small children.

In addition, slugs and snails pose a significant problem in rodent bait stations. They are attracted to the bait station and may eat the rodenticide, reducing the amount of bait available for rodents. They may also physically block rodent bait stations and reduce access to the bait. Worst of all, slugs and snails may eat rodenticides, and then in turn be eaten by birds or non-target small mammals, domestic pets, or small children which can potentially result in human fatality.

Therefore, a need exists for improved pest control formulations which are capable of controlling multiple forms of pests, including rodents, insects, and terrestrial mollusks.

SUMMARY

The disclosure relates to materials and methods for controlling rodents, insects, and terrestrial mollusks. In particular, the disclosure relates to a triple-action pest control formulation having at least two active pesticidal ingredients which in combination provide rodenticide, insecticide, and molluscicide activity, and preferably being resistant to mold formation and biodeterioration.

The present disclosure is directed to a pest control composition formulated to be attractive to, and consumed by, a range of rodent, arthropod, and terrestrial mollusk pest species, including rats and mice, insects, and snails and slugs. The physical and chemical formulation provides a bait with broad spectrum performance against numerous rodent pests, such as rats and mice, most insect pests as well as many general non-insect arthropod pests, and terrestrial mollusk pests, such as slugs and snails. The inventive formulation effectively prevents the problems of a single-target pest control substance being consumed by a non-target species, resulting in promoting a non-target species at the expense of the efforts to exterminate the targeted species.

The present disclosure, in certain embodiments, provides triple-action pest control formulations which include both a rodenticide and an insecticide/molluscicide to kill rodents, insects, and mollusks, and permits various target pests to simultaneously consume a toxic dose of the pest control formulation. In certain embodiments, the insecticide/molluscicide is preferably a borate. The present disclosure also preferably provides a pest control formulation that maintains effectiveness after exposure to high humidity because it reduces mold growth and other biodeterioration that would otherwise inhibit consumption of the formulation by rodent, arthropod, and/or mollusk pests. The disclosure also provides triple-action pest control formulations which offers a potential human health benefit over rodenticides or insecticides used in a home or within an enclosed environment by limiting exposure to mold and mold spores.

The pest control formulation of the present disclosure generally combines the following specific components: a rodenticide or rodenticidal active ingredient that is non-repellent to rodents, insects, and mollusks, and an insecticide/molluscicide or insecticidal/molluscicidal active ingredient in an amount that is non-repellant to rodents, insects, and mollusks. The insecticide/molluscicide desirably also serves as a rodent attractant, and can include a borate salt or another suitable borate such as boric acid. The formulation can also include a solid, a liquid, or granular carrier matrix, and one or more food attractants that serve to invite ingestion of the entire matrix and the active ingredients by both rodent, insect, and terrestrial mollusk pests. Suitable attractants can include, for example, any of mixed carbohydrates (including sugars), lipids, proteins, and combinations thereof.

More broadly, the disclosure includes a triple-action pest control formulation for controlling rodents, insects, and terrestrial mollusks, the formulation comprising a first active ingredient which is a rodenticide, a second active ingredient which is both an insecticide and a molluscicide, an attractant, and a carrier matrix. The first active ingredient can be, for example, a single dose anti-coagulant rodenticide. Alternatively, the first active ingredient can be, a multiple dose anti-coagulant rodenticide. This first active ingredient is typically substantially non-repellent to rodents, insects, and mollusks. Suitable rodenticides include, for example, colecalciferol, brodifacoum, bromadiolone, difethialone, warfarin, chlorophacinone, diphacinone, zinc phospide, bromethalin, and like compounds, or combinations thereof. Two particularly useful rodenticides are, for example, difethialone and bromadiolone.

Similarly, the second active ingredient is desirably substantially non-repellent to rodents, insects, and mollusks. The second active ingredient may, for instance, include a borate. Borates are particularly useful as both insecticides and molluscicides, and suitable "borates", as the term is used herein, include borax pentahydrate, borax decahydrate, disodium octaborate tetrahydrate, potassium pentaborate, boric acid, calcium borate, zinc borate, sodium calcium borate, colemanite, ulexite, tincal, and mixtures thereof. Borax (sodium borate) is especially useful in both pesticidal applications. In certain embodiments, the second active ingredient can include, for example, less than about 20 percent of a borate based upon total dry weight of the formulation, and in other embodiments, less than about 10 percent. Typically, when a borate is used, it is provided in an amount greater than about 2 percent of the total weight of the formulation. Lower levels of borates tend to result in less resistance to mold formation in the finished formulation. In embodiments, the percentage of borate can be, for example, from about 3 to about 8 percent by weight of the formulation.

The formulation may further include a third active ingredient which is a secondary insecticide. In certain embodiments, for instance, the secondary insecticide can include, for example, one or more of pyriproxyfen, methoprene, fenoxycarb, hydramethylnon, sulfluramid, fipronil, abamectin, propoxur, spinosad, and like compounds, or mixtures thereof. In certain other embodiments, the secondary insecticide includes an insect growth regulator.

The formulation can also generally include a carrier matrix. Suitable carrier matrices include, for example, ground corn cobs, or like particulate materials derived from corn cobs, waxes, or other like organic materials. The carrier matrix may include, for instance, a particulate of corn cob, corn starch, corn meal, corn flour, potato starch, potato meal, potato flour, rice, rice flour, nut meal, wax, or mixtures thereof. The formulation can also, in embodiments, include at least one attractant. In general, the attractant can include, for example, a carbohydrate, a lipid, or a protein. In embodiments, the attractant and the matrix can be the same material. In embodiments, the attractant and the matrix can be different or dissimilar materials.

The present disclosure is also directed to a method of controlling rodents, insects, and mollusks. In certain embodiments, the method includes providing a triple-action pest control formulation including an active ingredient which functions as both an insecticide and a molluscicide. The active ingredient is substantially non-repellent to rodents, insects, and mollusks and includes from about 2 to about 20 percent weight of a borate based upon the total dry weight of the pest control formulation. The formulation used in the method also includes a rodenticide that is substantially non-repellent to rodents, insects, and mollusks, and a carrier matrix. The formulation is applied to a target area in an amount effective to control rodents, insects, and mollusks. In certain embodiments, the pest control formulation may also include an attractant.

The rodenticide of the formulation can be, for example, difethialone, bromadiolone, and like compounds, or combinations thereof. In embodiments, the insecticide/molluscicide can include generally less than about 20 percent of a borate, and often less than about 10 percent of a borate, of the formulation by dry weight. The insecticide/molluscicide may include, for example, from about 2 to about 10 percent of a borate based upon the total dry weight of the formulation. In embodiments, the insecticide/molluscicide can include, for example, from about 3 to about 8 percent of a borate.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Rodenticide

Figure 1:
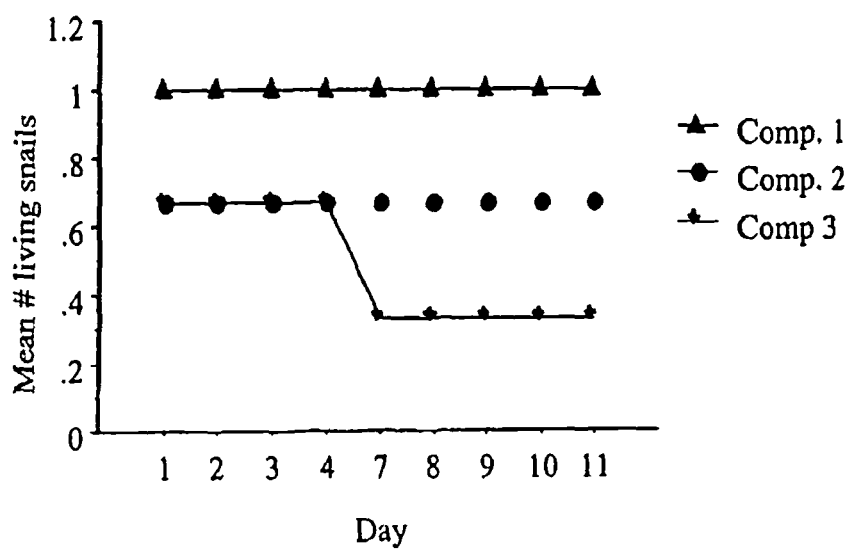
FIG. 1 is a chart showing the efficacy of formulations made in accordance with the invention at exterminating terrestrial mollusks.

Many rodenticides can be used as the first active ingredient to practice the present invention, including, for example, colecalciferol, brodifacoum, bromadiolone, difethialone, warfarin, chlorophacinone, diphacinone, zinc phospide, bromethalin, and like compounds, or mixtures thereof. A preferred rodenticide is, for example, a single dose anticoagulant, for which Vitamin K1 is a readily available antidote in case of accidental human or pet ingestion. The rodenticide can also be a multiple dose anticoagulant. Two particularly useful rodenticides are, for example, difethialone and bromadiolone. These rodenticides are desirable, in part, because they are effective against both rats and mice.

The rodenticide is desirably substantially non-repellant to rodents, insects, and mollusks. A rodenticide is substantially non-repellant to rodents, insects, and mollusks where most rodents, insects, and mollusks will consume at least some of a composition containing the rodenticide. Other rodenticides are known and include, for example, poisons such as arsenic, barium, barium carbonate, bromethalin, strychnine, tetramine, or thallium. Still other rodenticides include non-repellent non-anticoagulant compounds, such as disclosed in U.S. Pat. No. 6,689,796, and more recently sperm-count lowering or sterilant compounds, U.S. Pat. No. 4,287,183, to Hagerman et al., entitled "Method for Killing Rodents," mentions a rodenticide composition comprising a dry mixture of a first ingredient which is a substance that rodents are fond of eating (e.g., cornmeal), and a second ingredient which has the propensity to react with water and thereby transform to a hydrated cementitious solid aggregate (e.g., plaster of paris). The disclosures of these U.S. patents are incorporated herein by reference in their entirety.

Insecticide/Molluscicide

The formulation also includes a second active ingredient which is effective as both an insecticide and a molluscicide. The second active ingredient should be substantially non-repellant to rodents, insects, and mollusks. The second active ingredient is substantially non-repellant to rodents, insects, and mollusks where most rodents, insects, and mollusks will consume at least some of a composition containing the insecticide.

In this regard, borates are particularly useful as insecticides, and borax is an especially useful borate example. When borax is used, the pest control composition generally can include less than about 20 percent by weight borax based upon total dry weight of the formulation, and in certain embodiments less than about 10 percent by weight. Typically, when borax is used, the formulation can include greater than about 1 percent borax based upon total dry weight of the formulation. In certain embodiments. the percentage of borax can be, for example, from about 3 to about 8 percent by dry weight of the total formulation. For example, the insecticide may include borax pentahydrate, borax decahydrate, disodium octaborate tetrahydrate, potassium pentaborate, boric acid, calcium borate, zinc borate, sodium calcium borate, colemanite, ulexite, tincal, and mixtures thereof. The borate content can be, for example, from about 2% to about 10% boric acid equivalent loading of boric acid, borax or disodium octaborate tetrahydrate (DOT) on a dry weight percent basis (by comparing $B_2O_3$ content).

The second active ingredient is also effective as a molluscicide for controlling terrestrial mollusks, particularly snails and slugs, and borates are also suitable for this purpose. Thus, the second active ingredient may include, for example, boric acid and/or borax which acts as a molluscicide as well as an insecticide. To be suitable as a molluscicide, the second active ingredient, such as boric acid, represents at least 1 percent of the pest control formulation, based upon total dry weight of the pest control formulation. In some implementations, the boric acid optionally is present in an amount of from about 0.1 to about 10 percent of the pest control formulation based upon total dry weight of the pest control formulation. The amount of boric acid can be less than 20 percent in some embodiments, and less than 10 percent in certain embodiments, based upon total dry weight of the pest control formulation.

Advantageously, pest control formulations including borates made according to the present disclosure are generally durable under environmental conditions in which terrestrial mollusks thrive, including moist environments and environments with high humidity. Thus, the pest control formulation of the present invention desirably retains its physical integrity after being exposed to the weather (precipitation, UV light, heat, air oxidation, hydrolysis and leaching) for at least 1 week. Similarly, the pest control formulation has been observed to substantially retain its efficacy after being exposed to the weather (precipitation, UV light, air oxidation, hydrolysis and leaching) for 1 month under many circumstances. Although the formulation can be administered in various forms, it is advantageous to be administered to pests in a granular or pellet form of varying particle sizes to allow easy ingestion by a range of slug and snail and insect sizes and species. Alternatively, however, the bait can be provided as a solid block from which the portion of the material may be removed by the pest.

Secondary Insecticide

In addition to the insecticide/molluscicide, the formulation may also, optionally, include a third active ingredient which is a secondary insecticide. In this regard, various secondary insecticides may be used in accordance with the present disclosure, and include, for example, various insect growth regulators. The secondary insecticide desirably can be substantially non-repellent to both rodents and insects, and desirably can be relatively slow acting. The secondary insecticide selected can include, for example, a stomach poison, contact insecticide, insect growth regulator, and like insecticides, or combinations thereof, for example, one or more of pyriproxyfen, methoprene, fenoxycarb, hydramethylnon, sulfluramid, fipronil, abamectin, propoxur, spinosad, or mixtures thereof. In other embodiments, the insecticide can include an insect growth regulator, such as hydroprene, pyriproxyfen, fenoxycarb, or combinations thereof. The secondary insecticide is preferably of a sufficient concentration to realize insecticidal properties.

As an example of a secondary insecticide, U.S. Pat. No. 6,984,662, to Cottrell, et al., entitled "High Concentration Topical Insecticide Containing Insect Growth Regulator," mentions an insecticide formulation that contains both an insecticide and an insect growth regulator, the disclosure of which is incorporated herein by reference in its entirety.

Attractants

The pest control formulation can also optionally include one or more attractants. Lipids and carbohydrates are two particularly useful attractants used in the formulation of the disclosure. Two or more attractants or food sources within the formulation can be used to give the formulation a broader appeal by satisfying a variety of nutritional needs of various target pests. The use of two or more pest active ingredients along with multiple attractants together can provide synergistic performance in terms of total pest management. Many attractants are suitable and include, for example, oil, sugar, protein sources (e.g., yeast extract, soy, albumin, etc.), and carbohydrate sources (e.g., wheat, corn, oat, rice or potato flour, malt extract, etc.). For example, various lipids, corn oil, soy bean oil, peanut oil, animal derived fat, or mixtures thereof can be suitable attractants, in embodiments. The amount of attractant included in a formulation is selected so that pest species are adequately attracted to and consume the formulation. U.S. Pat. No. 4,581,378, issued Apr. 8, 1986, to Lazar et al., entitled "Rodenticide Compositions Comprising an Artificial Sweetener and a Rodenticide," discloses a food energy inhibitor for controlling rodents, such as rats and mice, which includes pellets of either crushed or dried corncobs, or spent grain bound together with an attractant, such as molasses, the disclosure of which is incorporated herein by reference in its entirety.

Carrier Matrix

The pest control formulation also generally includes a carrier matrix designed to give physical form and carry the attractants and active ingredients. The carrier matrix may also itself include an attractant. Many different carrier matrices are suitable including, for example, at least one of a flour or meal of a carbohydrate, lipid, or protein. Suitable carrier matrices can also include, for example, cellulose-based plant derived products, such as corn cobs, corn starch, corn meal, corn flour, potato starch, potato meal, potato flour, rice or rice flour, nut meal, and like materials, as well as wax or combinations thereof, or materials derived from any of these. In certain embodiments, the carrier matrix is blended with the other constituents of the formulation and baked, formed, or shaped to serve as a bait for the targeted pest.

The amount of carrier matrix in the formulation can be chosen so that the resulting formulation has desirable shape and mass for manufacture, packaging, handling, application, and pest consumption. For example, in one embodiment, a formulation may include about 80% by weight carrier matrices. U.S. Pat. No. 4,518,580, issued May 21, 1985, to Pasarela, entitled "Expanded Corncob Grits Having Increased Absorptivity and a Method for the Preparation thereof," provides an example matrix where the expanded grits, which possess increased absorptivity, are found to be useful in the formulation of insecticidal baits, especially fire ant baits, and other agricultural compositions. See also the abovementioned U.S. Pat. No. 4,581,378. The disclosures of the above U.S. patents are incorporated herein by reference in their entirety.

A suitable wax for the carrier matrix can be any mineral, plant, or animal derived wax substance including for example, natural wax, synthetic wax, or mixtures thereof, such as, slack wax from Exxon Corp. Other examples of suitable waxes include beeswax, paraffin wax, micro wax, microcrystalline wax, candellila wax, carnauba wax, rice wax, montan wax, polyethylene wax, polypropylene wax, copolyalkylene wax, oxidized polyalkylene wax, poly(alkylene oxide) wax, copoly(alkylene oxide) wax, and like substances, or mixtures thereof.

The use of two or more active ingredients provides the bait with a broader spectrum of performance. The use of multiple active ingredients and multiple attractants provides synergistic performance in overall pest management.

Methods and Materials of Formulation and Use

In certain embodiments, the ingredients used to make the triple-action pest control formulation can be mixed using various methods known to those skilled in the art. It is generally desirable to mix the components in a dry process that blends and combines the components and produces specific sized granules that can perform triple-action pest control for extended time periods. Alternatively, the materials can be mixed together as a dry or wet formulation, and then formed into pellets or into a solid block.

Thoroughly mixing the ingredients is preferred to partial mixing. In some embodiments, it is desirable that every particle of the formulation have activity against insects, rodents, and terrestrial mollusks. Thus, even if a particular pest preferentially selects particles of certain size, texture, or other physical characteristics, that pest will still be exterminated. If the formulation contains distinct particles that only contain one active ingredient, then one pest may selectively eat only that formulation that is not toxic to it, thereby reducing efficacy of pest control measures. Also, in some circumstances it is possible to have the particles separate from one another during shipping or packaging, due to for example particle size or density differences or sorting, thereby limiting the effectiveness of the formulation if one of the active ingredients is not readily accessible because the particles containing it have settled to the bottom of a package or application device. Although it is generally desirable that the active ingredients be combined within each individual particle, the formulation may still be effective where the active ingredients are combined within the formulation but on different individual particles in the formulation if the target pests consume a sufficient quantity of the target insecticide or rodenticide that is toxic to them.

It has been discovered that different pests sometimes require different particle sizes for the formulation to be effective. For example, insects, especially ants, sometimes prefer to consume particles of granular sizes that are within the range of about #8 Mesh to about #100 Mesh and particularly prefer particles of granular sizes that are within the range of about #14 Mesh to about #80 Mesh. This particle size range has also been found to provide ample foraging opportunities for many different insect species and size ranges, such as cockroaches, silverfish, crickets, numerous species of ants (including fire ants, argentine ants, odorous house ants, carpenter ants, and pavement ants), and can still be eaten by rodents. After formulation, such as by agglomerative binding, rodents and especially insects can remove their preferred particle size from a larger solid particle with relative ease.

In certain embodiments, a combined sandwich approach can also be used to deliver the active ingredients of the disclosure. In such implementations, a rodenticide is formed separately from an insecticide/molluscicide, and then the rodenticide and the insecticide/molluscicide (along with any secondary insecticide) are intimately joined together to form a sandwich or layered structure. Such a physical formulation is best carried out with solid forms. Solid forms or solid formulations, such as monolith or block formation, can be accomplished in many ways known to those skilled in the art by, for example, solidifying a liquid or solidifying a granular material into an aggregate or like mass with a suitable binder, using for example, agar (available from Oxoid), animal or vegetable derived gelatin, long chain polyalkylene glycols (available from Dow Chemical), waxes, natural or synthetic resins, and like methods and materials, or combinations thereof.

The disclosure is also directed to a method of controlling rodents, insects, and terrestrial mollusks. The method comprises providing a triple-action pest control formulation for rodents, insects, and terrestrial mollusks, the triple-action pest control formulation comprising a rodenticide that is substantially non-repellent to rodents, insects, and terrestrial mollusks, and an insecticide/molluscicide that is substantially non-repellent to rodents, insects, and terrestrial mollusks. The insecticide/molluscicide includes from about 2 to about 20 percent borax based upon the total dry weight of the pest control formulation; and a carrier matrix. The rodenticide of the triple-action pest control formulation can be, for example, difethialone, bromadiolone, and like rodenticides, or combinations thereof.

The following nonlimiting examples illustrate various additional aspects of the invention. Unless otherwise indicated, temperatures are in degrees Celsius and percentages are by weight based on the dry weight of the formulation.

EXAMPLE FORMULATIONS

Example 1

One illustrative formulation for pest control has about 39% by weight slack wax (available from Exxon) and about 30% ground corncob as a carrier matrix, about 10% corn oil and about 15% sugar as attractants, about 5% borax as an insecticide, and about 0.005% bromadiolone as a rodenticide, based on the total weight of the formulation.

The components can be blended together in an essentially dry process that intimately combines the components to produce specific sized granules that can perform in pest (rodent, arthropod, and mollusk) abatement for extended time periods, for example, from about 1 to about 12 months, or longer. The powdered sugar, borate and bromadiolone are added to the corn cob and pre-mixed in a Marion mixer ribbon blended for about 5 to about 10 minutes. To this mixture is added the corn oil and wax and mixing continued for about an additional 20 to 25 minutes. Heat can optionally be applied to melt and distribute the wax as a binding agent. A wet process with an alternative binder material, for example, agar, gelatin, albumin, and like materials, or mixtures thereof, can also optionally be selected. The binder can be used to conveniently produce molded solid forms of the disclosure, such as a cake or bar, from which granules can be easily broken off from the solid form by a feeding pest.

Example 2

EPA Diet. Yet another illustrative formulation is the EPA test formulation diet and consists of the ingredients in the amounts shown Table 1.

TABLE 1

EPA Test Formulation Diet.

| Ingredient | % by weight |
|---|---|
| Cornmeal (whole yellow ground corn) | 65 |
| Rolled oat groats (ground) | 25 |
| Sugar (10x powdered or confectioners, 95% + purity) | 5 |
| Corn oil (95% + purity) | 5 |

The EPA diet is also referred to as the "EPA challenge diet" see for example, "EPA 1991. Standard House Mouse Acute Dry Bait Laboratory Test Method. OPP Designation: 1.210 Revision No. 9. USEPA." The EPA challenge diet was prepared by Genesis Laboratories of Wellington, Colo. (www.genesislabs.com) by combining the solid ingredients, adding the corn oil, and then mixing thoroughly with utensils in vessels that were free of contamination. The diet could be readily modified further with the addition of one or more toxicants, such as described below.

Experimental Results

Example 3

The purpose of this study was to determine the acceptance and consumption rate by laboratory mice (*Mus musculus*) of diet formulations of the disclosure having borate and comparison diet formulations free of borate, after the diet formulations had been exposed to high humidity, for example, of about 50-55% relative humidity or higher, during incubation at about 20 to about 25° C. for two months. Each of four experimental diets (Diets A-D) were formulated from the abovementioned EPA challenge diet formulation and were simultaneously presented to twelve mice and evaluated for acceptability during a 3-day diet presentation period. Diet A contained 2.5% by weight boric acid equivalent (BAE) Borax and was not exposed to high humidity. Diet B contained 2.5% BAE Borax and was exposed to high humidity. Diet C was a humidity control that contained no borate and was exposed to high humidity. Diet D was a fresh control that contained no borate and was not exposed to high humidity. Mold grew on the incubated diet formulations at elevated humidities although to different extents. The extent of mold growth appeared to depend upon the diet composition. The diets that included a borate appeared to inhibit mold growth and improved the palatability and consumption of incubated diets.

Twelve mice (6 male, 6 female) were evaluated for the test diets. Mice were housed in double-wide cages measuring 24×40.5×18 cm (L×W×H) with a floor area of least 972 $cm^2$. Tap water in glass bottles with stainless steel sipper tubes were available ad libitum. The cages were suspended from shelves on two single-sided racks. Mice were placed in cages identified by a consecutive number 1-12 and a descriptor for their sex (e.g., M or F).

The diets were modified by adding borates as indicated to the EPA challenge diet and then exposing the diets to high humidity to produce the four diets (Diets A-D). On the morning of the experimental set up, all maintenance diet rodent pellets were removed from each cage. Glass feed cups were used to present the four test diets to each mouse to determine if there was preference for any one diet. The feed cups were labeled with the cage number and treatment diet. The cups were placed along the front of the cage and the cup positions were rotated throughout the test period to prevent positional bias. The results of the acceptance test appear in Table 2.

TABLE 2

Diet acceptance test results

| Mouse Number and Sex | Total Test Diet A (borate) Consumed (g) | Total Test Diet B (borate + humidity) Consumed (g) | Total Test (humidity) Consumed (g) | Total Test (control) Consumed (g) | Total Diet Comsumed (g) |
|---|---|---|---|---|---|
| 1F | 3.2 | 9.4 | 10.0 | 18.8 | 41.4 |
| 2F | 4.3 | 4.5 | 6.6 | 26.1 | 41.5 |
| 3F | 12.1 | 12.9 | 6.7 | 14.7 | 46.4 |
| 4F | 12.3 | 7.0 | 1.8 | 12.4 | 33.5 |
| 5F | 7.6 | 4.5 | 0.0 | 16.8 | 28.9 |
| 6F | 6.5 | 12.4 | 11.4 | 22.4 | 52.7 |
| 7M | 12.8 | 17.6 | 1.0 | 13.7 | 45.1 |
| 8M | 8.4 | 20.4 | 6.2 | 20.9 | 55.9 |
| 9M | 11.0 | 0.3 | 1.5 | 14.0 | 26.8 |
| 10M | 9.9 | 1.6 | 0.3 | 6.8 | 18.6 |
| 11M | 16.1 | 1.5 | 1.0 | 14.4 | 33.0 |
| 12M | 24.3 | 5.3 | 1.8 | 13.4 | 44.8 |
| Total (g) | 128.5 | 97.4 | 48.3 | 194.4 | 468.6 |
| Percent Consumed | 27.4% | 20.8% | 10.3% | 41.5% | 100.0% |

The results demonstrate the effectiveness of the formulations as a bait for rodents such as mice. The mice on average consumed Diet A at 27.4% of total consumption, Diet B at 20.8%, Diet C at 10.3%, and the Control Diet D at 41.5%. This study shows a statistical preference (Fisher's PLSD, $p=0.05$) for ambient humidity exposed and fresh bait (Diet A and Diet D) over humidity exposed bait (Diet B and Diet C). This study also shows a statistical preference (paired t-test, $p=0.05$) for bait formulated with borate compared to bait without borate when exposed to high humidity (Diet B and Diet C). Although not measured, the diets without a borate probably had higher mold or bacterial growth which could produce the observed anti-feedant properties.

Example 4

Effectiveness as a Molluscicide

The following test was conducted to confirm the efficacy of formulations made in accordance with the invention on exterminating snails and slugs. Snails and slugs were collected from outdoors in Knox County, Tenn. Snails, slugs and water soaked cotton pads were placed in a disposable plastic container at the start of the study. A total of three or four snails and slugs, consisting of zero to one snail and two to three slugs, were placed in each of nine 739 ml disposable plastic containers. An 8 cm disposable petri dish, which held wet cotton and 1.6 gm granular bait treatment, was also placed in each container. Granular bait treatments consisted of a carrier material and attractant without a molluscicide, a carrier material and attractant with boric acid active ingredient, plus a carrier material, attractant, and iron phosphate (an industry standard molluscicide). When the composition was formulated with iron phosphate or without any pesticide, the percentage of inert ingredients was increased accordingly.

Figure 2:
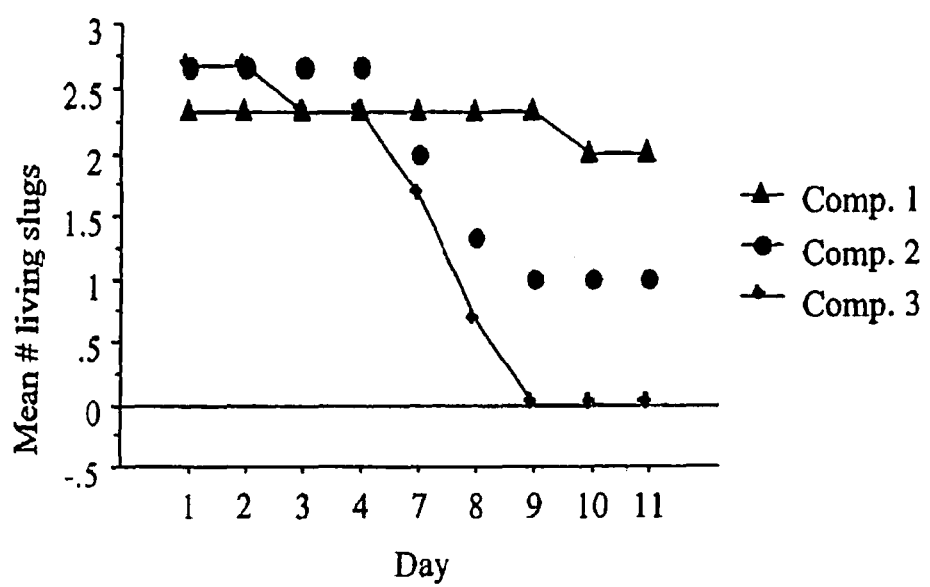
FIG. 2 is a second chart showing the efficacy of formulations made in accordance with the invention at exterminating terrestrial mollusks.
Figure 3:
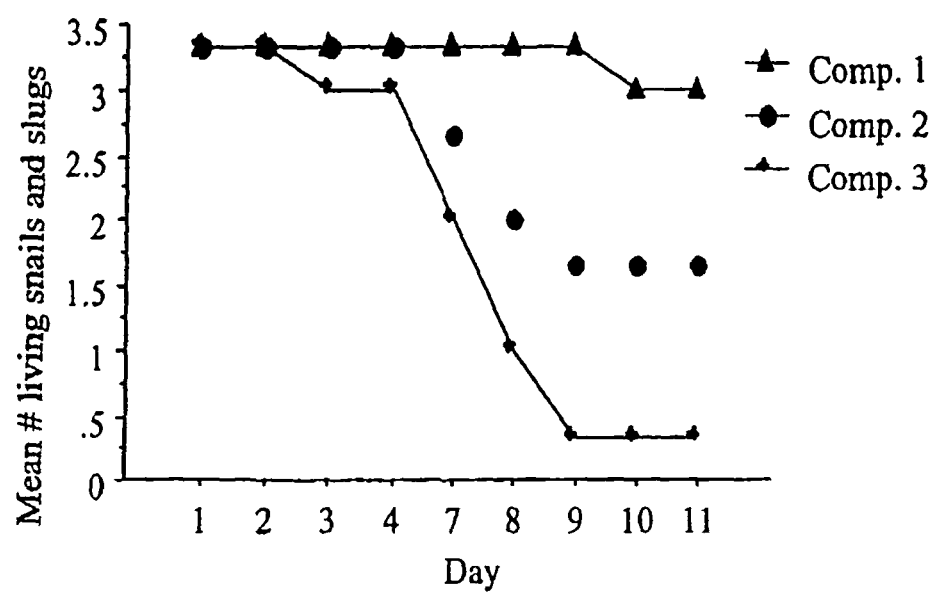
FIG. 3 is a third chart showing the efficacy of formulations made in accordance with the invention at exterminating terrestrial mollusks.

The results of this study are shown below in FIGS. 1, 2, and 3. FIG. 1 shows the mean number of living snails observed after eleven days of exposure to 1.6 grams of granular bait treatments. The first composition contained a control with only food attractants, while the second composition contained 1 percent $FePO_4$, and the third composition contained five percent $H_3BO_3$. FIG. 2 shows the mean number of living slugs observed alter eleven days of exposure to 1.6 grams of granular bait treatments. The first composition contained a control with only food attractants, while the second composition contained 1 percent $FePO_4$, and the third composition contained five percent $H_3BO_3$. FIG. 3 combines the results of FIGS. 1 and 2 and shows the mean number of living snails and slugs observed after eleven days of exposure to 1.6 grams of granular bait treatments. The first formulation contained a control with only food attractants, while the second composition contained 1 percent $FePO_4$, and the third composition contained five percent $H_3BO_3$.

The results show that boric acid was more effective than iron phosphate and the control at killing snails and slugs. On day 11 the mean number of living slugs and snails were 0 and 0.3, respectively. By day 7, the control bait and the iron phosphate bait had gone moldy while the boric acid bait had not. Published studies have also indicated that snail and slug baits go moldy in a short period of time (Hata, T. Y., A. H. Hara, and B. K. S. Hu. 1997, Molluscicides and mechanical barriers against slugs, *Vaginula plebeian* Fischer and *Veronicella cubensis* (Pfeiffer) (Stylommatophora: Veronicellidae). Crop-prot, 16 (6): 501-506). It was also discovered that the borate prevented the bait from going moldy throughout the duration of this study and this is seen as an additional benefit of the invention. This evaluation determined that boric acid has molluscicidal properties and that the proposed composition is an effective attractant to snails and slugs. A snail and slug bait containing boric acid is also likely to be more effective and last longer than other snail and slug baits available due to its fungicidal properties.

Example 5

Weather Testing Study

Weatherized granular bait made in accordance with the invention was tested in exposed exterior situations for a period of one month to determine its ability to withstand weathering conditions typical of the environment of snails and slugs. The active ingredient concentration in the bait was determined and plotted against the recorded amount of rainfall over the exposed period as well as exposure over time.

The granular bait used in this weathering test contained about 5% boric acid as the active ingredient and a combination of both lipid and carbohydrate attractants. The objective of this study was to determine the effectiveness of this process and the longevity of product performance by determining the rate of active ingredient loss due to exterior exposure. Three open stations, each containing 100-grams of the granular bait product and a perforated base were placed outside in 3 different open locations. A sample was taken from each station at regular intervals and the total rainfall was recorded using a rain gauge. This continued for about 1 month and until a total of >6 inches of rain had passed though the granular bait.

Following exposure, samples were oven dried at 35 degrees Celsius overnight. 5 grams of each sample was then taken and placed into 245 grams of water in a round bottom flask. This gave a dilution factor of 50. The flask was connected to a condenser and refluxed for 30 minutes to solubilize all available borate. The heat source was then removed and the flask allowed to cool with an inverted small beaker on the top of the condenser. Once cooled, the contents of the flasks were filtered using a Whatman 541 paper and the filtrate was analyzed for boric acid content using a standard mannitol titration. A suitable aliquot of the extract was taken and weighed (W). Dilute hydrochloric acid was added to lower the pH to 3 or 4, then 0.05M sodium hydroxide was added until a pH of 5.8 was reached, and burette reading noted. Excess mannitol (15 grams) was then added to the flask, and this was titrated back to 5.8 with 0.05M sodium hydroxide, again noting the burette reading. The concentration of borate as % boric acid equivalent (BAE) was then determined using the following calculation:

$$\% \text{ BAE} = (\text{Titre}/W) \times M \times 6.1823 \times 50$$

where Titre (total volume of NaOH used)=R1-R2, M is the molarity of the sodium hydroxide titrant, and 50 is the aforementioned dilution factor.

The analytical results have been shown against rainfall in Table 3 and against time in Table 4.

TABLE 3

Active Ingredient Content Compared to Rainfall

| Sample | Rainfall (inches) | % BAE |
|---|---|---|
| 1 | 0 | 4.7, 4.8, 4.8 |
| 2 | 0.3 | 4.8, 4.7, 4.8 |
| 3 | 0.4 | 4.7, 4.6, 4.7 |
| 4 | 0.6 | 4.7, 4.7 |
| 5 | 1.2 | 4.6, 4.6 |
| 6 | 1.3 | 3.5, 3.7, 3.7 |
| 7 | 2.5 | 0.8, 0.7, 0.8 |
| 8 | 6 | 0.04, 0.04 |

TABLE 4

Active Ingredient Content compared to Time

| Time (days) | % BAE |
|---|---|
| 0 | 4.7, 4.8, 4.8 |
| 2 | 4.8, 4.7, 4.8 |
| 7 | 4.7, 4.6, 4.7 |
| 14 | 4.7, 4.7 |
| 21 | 4.6, 4.6 |
| 23 | 3.5, 3.7, 3.7 |
| 25 | 0.8, 0.7, 0.8 |
| 27 | 0.04, 0.04 |

From these results it can be observed that the boric acid in the granular bait is slowly lost with increasing amounts of rainfall. From referring to various efficacy studies with a variety insects, boric acid is known to be effective below 0.5% retention. Light rainfall that does not soak right through the sample did not appear to significantly affect the boric acid content of the bait, and this is probably the case as the sample simply gets wet and then dries out again. However, a heavy downpour of at least 2 inches significantly reduces the boric acid content. This probably occurs as free running water passes through the bait, both solubilizing and removing the boric acid.

From the table of the same retention data compared to time rather than rainfall (Table 4), it can be seen that simple exposure to air and sunlight did not correlate with borate loss.

It can be concluded from this work that performance of the granular bait would be maintained for an extended period of time in the absence of rainfall and for up to 4 inches of accumulated rainfall. It is therefore recommended that re-application of the granular bait be carried out after any period of continuous 2 inches of rainfall, 4 inches of total rainfall, or 3 months, whichever occurred first.

Example 6

In this study, the efficacy of loose grain bait prepared according to the present disclosure was first examined in laboratory house mice (*Mus musculus*). A bait was prepared for use in the study containing corn, oats, oil, and sugar in accordance with the EPA challenge diet. In addition, the bait was formulated with 250 ppm brodifacoum as a rodenticide and 5%, by weight, of boric acid as an insecticide/molluscicide. A control bait was also prepared containing corn, oats, oil, and sugar in accordance with the EPA challenge diet, but without the rodenticide or the insecticide/molluscicide active ingredients.

For the study, six house mice, all males, were obtained and divided into two groups. Mice numbers 1, 3, and 5 were placed in the control group and fed the control bait with no active ingredients. Mice numbers 2, 4, and 6 were fed the bait according present disclosure with brodifacoum and boric acid. The mice were fed the aforementioned baits on a "no-choice" basis for three days, i.e., no other food sources were provided to the mice during this time. Each day, the amount of bait consumed was record. After three days, the aforementioned baits were removed and the mice were observed for an additional four days during which time water, but not additional food, vided to the mice. The results are summarized in the following table:

TABLE 5

Effectiveness against rodents

| Animal No. | Day 1 (g) | Day 2 (g) | Day 3 (g) | 3 Day Total (g) | Daily Ave. (g) | Date of Animal Death |
|---|---|---|---|---|---|---|
| 1 | 3.1 | 3.7 | 6.4 | 13.2 | 4.4 | na |
| 3 | 4.2 | 5.7 | 6.5 | 16.4 | 5.47 | na |
| 5 | 3.5 | 6.8 | 9.6 | 19.9 | 6.63 | na |
| 2 | 3.0 | 5.9 | 3.6 | 12.5 | 4.17 | Day 5 |
| 4 | 4.2 | 10.8 | 1.9 | 16.9 | 5.63 | Day 6 |
| 6 | 2.6 | 4.5 | 4.4 | 11.5 | 3.83 | Day 6 |

As can be seen from these results, the mice which were fed the bait formulation according to the present disclosure (Nos. 2, 4, 6) readily accepted the bait and consumed only slightly less food during the three days than the mice which were feed the control bait (Nos. 1, 3, 5). In addition, it was observed that all three mice which were fed the bait formulation according to the present disclosure died after either 5 or 6 days while none of the control mice died or otherwise showed any ill effects from consuming the control bait formulation.

The effectiveness of the same bait formulation was then tested with crickets. In this test, a first group of 27 crickets was fed the test bait with 250 ppm brodifacoum and 5% of boric acid for a total of three days. A second group of 27 crickets was fed the control bait without any brodifacoum or boric acid for the same three day time period. The crickets were periodically observed over this time period to determine is any of the has died The total number of dead crickets observed was as follows:

TABLE 6

Effectiveness against insects

| Time of Observation | Control Bait (no boric acid & no rodenticide) | Bait w/5% boric acid & 250 ppm brodifacoum |
|---|---|---|
| Day 0 (start) | 0 dead crickets | 0 dead crickets |
| Day 2 | 0 dead crickets | 17 dead crickets |
| Day 3 | 0 dead crickets | 27 dead crickets |

From these results, it may be seen that the bait formulation was readily consumed by the crickets, which are representative insect pests, and that the bait formulation was completely effective in killing the crickets.

The effectiveness of the same bait formulation was then tested a third time with terrestrial mollusks. The banded slug (*Limax marginatus*) was used in the tests as a representative species.

For this test, a total of 8 plastic tubs were partially filled with soil to provide with moist soil to provide an environment for slug testing. Each plastic tub had an overall volume of 6 quarts and was partially filled with potting soil. A mesh screen lid was also placed over each tub.

Ten banded slugs were placed in each tub along with 10 grams of bait formulation. In four of the tubs, the test bait formulation was used with 250 ppm brodifacoum and 5%, by weight, boric acid. In the four remaining tubs, the control formulation was used without any brodifacoum or boric acid. In all cases, the bait was placed in a Petri dish within the plastic tub. During the test, the plastic tubs were kept inside a warehouse with skylights to provide indirect sunlight and with temperatures ranging from 41° F. to 77° F. The plastic tubs were observed for a total of 28 days with the morality rate of the slugs being counted after 1 day, 3 days, 7 days, 14 days, and 28 days. The observed results were as follows:

TABLE 7

Effectiveness Against Slugs

| Tub | Slug Mortality After: | | | | |
|---|---|---|---|---|---|
| | 1 Day | 3 Days | 7 Days | 14 Days | 28 Days |
| Control 1 | 0 | 0 | 0 | 0 | 2 |
| Control 2 | 0 | 0 | 0 | 1 | 1 |
| Control 3 | 0 | 0 | 0 | 0 | 1 |
| Control 4 | 0 | 0 | 0 | 0 | 2 |
| Control Average (%) | 0% | 0% | 0% | 2.5% | 15% |
| Test 1 | 1 | 1 | 1 | 5 | 8 |
| Test 2 | 0 | 0 | 0 | 4 | 7 |
| Test 3 | 0 | 0 | 1 | 5 | 6 |
| Test 4 | 0 | 0 | 0 | 5 | 7 |
| Test Average (%) | 2.5% | 2.5% | 5% | 47.5% | 70% |

These results demonstrate that the test formulation was highly effective in eradicating the slugs. After 14 days, nearly half of the slugs which had been fed the test formulation were dead. After 28 days, 70% were dead. In comparison, only 2.5% of the slugs in the control were dead after 14 days and only 15% after 28 days.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A triple-action granular pest control formulation for controlling rodents, insects, and terrestrial mollusks, the formulation comprising:
   about 50 ppm of a first active ingredient which is a rodenticide comprising brodifacoum;
   a second active ingredient which is both an insecticide and a molluscicide comprising greater than about 2 percent and up to about 20 percent of a borate based upon total dry weight of the formulation;
   an attractant; and
   a granular carrier matrix.

2. The triple-action pest control formulation of claim 1, wherein the first active ingredient is substantially non-repellent to rodents, insects, and mollusks.

3. The triple-action pest control formulation of claim 1, wherein the first active ingredient further comprises a rodenticide selected from the group consisting of colecalciferol, bromadiolone, difethialone, warfarin, chlorophacinone, diphacinone, zinc phospide, bromethalin, and combinations thereof.

4. The triple-action pest control formulation of claim 1, wherein the first active ingredient further comprises difethialone.

5. The triple-action pest control formulation of claim 1, wherein the first active ingredient further comprises bromadiolone.

6. The triple-action pest control formulation of claim 1, wherein the second active ingredient is substantially non-repellent rodents, insects, and mollusks.

7. The triple-action pest control formulation of claim 1, wherein the second active ingredient comprises less than about 20 percent of a borate based upon total dry weight of the formulation.

8. The triple-action pest control formulation of claim 1, wherein the active ingredient comprises less than about 10 percent of a borate based upon total dry weight of the formulation.

9. The triple-action pest control formulation of claim 1, wherein the active ingredient comprises from about 3 to about 8 percent of a borate.

10. The triple-action pest control formulation of claim 1, wherein the second active ingredient is selected from the group consisting of borax pentahydrate, borax decahydrate, disodium octaborate tetrahydrate, potassium pentaborate, boric acid, calcium borate, zinc borate, sodium calcium borate, colemanite, ulexite, tincal, and mixtures thereof.

11. The triple-action pest control formulation of claim 1, wherein the carrier matrix comprises a particulate of corn cob, corn starch, corn meal, corn flour, potato starch, potato meal, potato flour, rice, rice flour, nut meal, wax, or mixtures thereof.

12. The triple-action pest control formulation of claim 1, wherein the attractant comprises a carbohydrate, a lipid, a protein, or combinations thereof.

13. The triple-action pest control formulation of claim 1, wherein the formulation inhibits mold growth and the formulation resists biodeterioration.

14. The triple-action pest control formulation of claim 1, further comprising a third active ingredient which a secondary insecticide.

15. The triple-action pest control formulation of claim 14, wherein the secondary insecticide is an insect growth regulator.

16. The triple-action pest control formulation of claim 14, wherein the secondary insecticide is selected from the group consisting of pyriproxyfen, methoprene, fenoxycarb, hydramethylnon, sulfluramid, fipronil, abamectin, propoxur, spinosad, hydroprene, and mixtures thereof.

17. A triple-action pest control formulation comprising:
   an active ingredient which functions as both an insecticide and a molluscicide, wherein the active ingredient is substantially non-repellent to rodents, insects, and mollusks and comprises from about 2 to about 20 percent weight of a borate based upon the total dry weight of the pest control formulation;
   about 50 ppm of a rodenticide comprising brodifacoum that is substantially non-repellent to rodents, insects, and mollusks; and
   a granular carrier matrix.

18. The triple-action pest control formulation of claim 17, wherein the active ingredient comprises from about 2 to about 10 percent of a borate based upon total dry weight of the formulation.

19. The triple-action pest control formulation of claim 17, wherein the active ingredient comprises from about 3 to about 8 percent of a borate.

20. The triple-action pest control formulation of claim 17, further comprising an attractant.

21. The triple-action pest control formulation of claim 20, wherein the attractant comprises mixed carbohydrates, lipids, or proteins.

22. A method of controlling rodents, insects, and mollusks comprising the steps of:
   providing a triple-action pest control formulation including an active ingredient which functions as both an insecticide and a molluscicide, wherein the active ingredient is substantially non-repellent to rodents, insects, and mollusks and comprises from about 2 to about 20 percent weight of a borate based upon the total dry weight of the pest control formulation; about 50 ppm of a rodenticide comprising brodifacoum that is substantially non-repellent to rodents, insects, and mollusks; and a granular carrier matrix; and
   applying the triple action pest formulation to a target area in an amount effective to control rodents, insects, and mollusks.

23. The method of controlling rodents, insects, and mollusks of claim 22, wherein the insecticide comprises from about 2 to about 10 percent of a borate based upon total dry weight of the formulation.

24. The method of controlling rodents, insects, and mollusks of claim 22, wherein the insecticide comprises from about 3 to about 8 percent of a borate.

25. The method of controlling rodents, insects, and mollusks of claim 22, wherein the triple-action pest control formulation further comprises an attractant.

* * * * *